(12) United States Patent
Ito et al.

(10) Patent No.: US 10,551,322 B2
(45) Date of Patent: *Feb. 4, 2020

(54) SURFACE-ENHANCED RAMAN SCATTERING UNIT INCLUDING INTEGRALLY FORMED HANDLING BOARD

(71) Applicant: HAMAMATSU PHOTONICS K.K., Hamamatsu-shi, Shizuoka (JP)

(72) Inventors: Masashi Ito, Hamamatsu (JP); Katsumi Shibayama, Hamamatsu (JP); Toshimitsu Kawai, Hamamatsu (JP); Kazuto Ofuji, Hamamatsu (JP); Hiroki Oyama, Hamamatsu (JP); Yoshihiro Maruyama, Hamamatsu (JP); Takafumi Yokino, Hamamatsu (JP); Masaki Hirose, Hamamatsu (JP); Anna Yoshida, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/420,483

(22) PCT Filed: Aug. 9, 2013

(86) PCT No.: PCT/JP2013/071703
§ 371 (c)(1),
(2) Date: Feb. 9, 2015

(87) PCT Pub. No.: WO2014/025034
PCT Pub. Date: Feb. 13, 2014

(65) Prior Publication Data
US 2015/0233830 A1    Aug. 20, 2015

(30) Foreign Application Priority Data

Aug. 10, 2012 (JP) ................. 2012-178766
Mar. 29, 2013 (JP) ................. 2013-073312

(51) Int. Cl.
*G01N 21/65* (2006.01)
*B82Y 40/00* (2011.01)

(52) U.S. Cl.
CPC ............ *G01N 21/658* (2013.01); *B82Y 40/00* (2013.01); *G01N 2021/651* (2013.01)

(58) Field of Classification Search
CPC ............... G01N 21/65; G01N 21/658; G01N 2021/651; G01N 21/8483; G01N 21/554
See application file for complete search history.

(56) References Cited

U.S. PATENT DOCUMENTS

| 5,655,661 A | 8/1997 | Rigby |
| 6,582,996 B1 | 6/2003 | Hara et al. |

(Continued)

FOREIGN PATENT DOCUMENTS

| CN | 1563989 | 1/2005 |
| CN | 1957245 | 5/2007 |

(Continued)

OTHER PUBLICATIONS

"Q-SERS™ G1 Substrate," Opto Science, Inc. (retrieved on-line on Jul. 5, 2013).

(Continued)

*Primary Examiner* — Dominic J Bologna
*Assistant Examiner* — Violeta A Prieto
(74) *Attorney, Agent, or Firm* — Drinker Biddle & Reath LLP

(57) ABSTRACT

A SERS unit comprises an integrally formed handling board and a SERS element secured within a container space provided in the handling board so as to open to one side in a thickness direction of the handling board. The SERS element has a substrate arranged on an inner surface of the (Continued)

container space and an optical function part formed on the substrate, for generating surface-enhanced Raman scattering.

13 Claims, 11 Drawing Sheets

(56) References Cited

U.S. PATENT DOCUMENTS

| | | | |
|---|---|---|---|
| 7,545,490 | B1 | 6/2009 | Pendell-Jones |
| 9,851,305 | B2 * | 12/2017 | Ito ..................... G01N 21/658 |
| 2004/0023046 | A1 | 2/2004 | Schlottig et al. |
| 2005/0224253 | A1 | 10/2005 | Aoki et al. |
| 2006/0034729 | A1 * | 2/2006 | Poponin .............. G01N 21/658 422/82.05 |
| 2006/0061762 | A1 | 3/2006 | Dwight et al. |
| 2006/0146323 | A1 | 7/2006 | Bratkovski et al. |
| 2006/0164637 | A1 * | 7/2006 | Wang ..................... B82Y 20/00 356/301 |
| 2007/0140900 | A1 | 6/2007 | Wang et al. |
| 2007/0252983 | A1 | 11/2007 | Tong et al. |
| 2007/0254377 | A1 | 11/2007 | Li et al. |
| 2008/0094621 | A1 | 4/2008 | Li et al. |
| 2008/0174775 | A1 | 7/2008 | Moskovits et al. |
| 2008/0218761 | A1 | 9/2008 | Nishikawa et al. |
| 2009/0108181 | A1 * | 4/2009 | Ishihara ............ H01L 27/14623 250/214.1 |
| 2009/0137411 | A1 * | 5/2009 | Sun .................. G01N 33/54366 506/9 |
| 2009/0231586 | A1 * | 9/2009 | Murakami ........... G01N 21/658 356/432 |
| 2010/0009456 | A1 * | 1/2010 | Prins ................... G01N 33/558 436/164 |
| 2010/0321684 | A1 | 12/2010 | Bratkovski et al. |
| 2011/0027901 | A1 | 2/2011 | Gaster et al. |
| 2011/0116089 | A1 | 5/2011 | Schmidt et al. |
| 2011/0166045 | A1 | 7/2011 | Dhawan et al. |
| 2011/0194116 | A1 * | 8/2011 | Horiuchi ................ G01N 21/13 356/445 |
| 2011/0267606 | A1 | 11/2011 | Ou et al. |
| 2012/0086021 | A1 | 4/2012 | Wang |
| 2012/0265038 | A1 | 10/2012 | Kawamura et al. |
| 2014/0043605 | A1 | 2/2014 | Tseng et al. |
| 2014/0218727 | A1 * | 8/2014 | Li ....................... G01N 21/658 356/301 |
| 2015/0204792 | A1 * | 7/2015 | Shibayama .......... G01N 21/658 356/301 |
| 2016/0054227 | A1 * | 2/2016 | Ito ...................... G01N 21/658 356/301 |

FOREIGN PATENT DOCUMENTS

| | | |
|---|---|---|
| CN | 101281133 | 10/2008 |
| CN | 101319994 | 12/2008 |
| CN | 101523212 | 9/2009 |
| CN | 101936906 | 1/2011 |
| CN | 102282094 | 12/2011 |
| CN | 102183354 | 5/2012 |
| CN | 102590088 | 7/2012 |
| CN | 103930780 | 7/2014 |
| CN | 104011520 | 8/2014 |
| EP | 2101166 | 9/2009 |
| GB | 2436719 | 10/2007 |
| JP | H05-044867 U | 6/1993 |
| JP | H07-260646 A | 10/1995 |
| JP | 2003-026232 A | 1/2003 |
| JP | 2005-337771 A | 12/2005 |
| JP | 2005337771 A * | 12/2005 |
| JP | 2006-208271 | 8/2006 |
| JP | 2006-250924 | 9/2006 |
| JP | 2007-530925 A | 11/2007 |
| JP | 2007-538264 A | 12/2007 |
| JP | 2008-064574 | 3/2008 |
| JP | 2008-519254 A | 6/2008 |
| JP | 2008-196992 A | 8/2008 |
| JP | 2008-268059 A | 11/2008 |
| JP | 2009-025316 A | 2/2009 |
| JP | 2009-047623 A | 3/2009 |
| JP | 2009-103643 A | 5/2009 |
| JP | 2009-222401 A | 10/2009 |
| JP | 2009-222507 A | 10/2009 |
| JP | 2009-236830 A | 10/2009 |
| JP | 2009-544967 A | 12/2009 |
| JP | 2010-506191 A | 2/2010 |
| JP | 2010-230352 | 10/2010 |
| JP | 2011-021085 | 2/2011 |
| JP | 2011-033518 A | 2/2011 |
| JP | 2011-506916 A | 3/2011 |
| JP | 2011-075348 A | 4/2011 |
| JP | 2011-107032 A | 6/2011 |
| JP | 2011-141265 A | 7/2011 |
| JP | 2011-201769 | 10/2011 |
| JP | 2011-215021 A | 10/2011 |
| JP | 2012-063293 | 3/2012 |
| JP | 2012-132875 A | 7/2012 |
| JP | 2012-233707 A | 11/2012 |
| TW | 201229490 | 7/2012 |
| WO | WO-2007/134191 A1 | 11/2007 |
| WO | WO-2007/149120 A2 | 12/2007 |
| WO | WO 2009/119391 A | 10/2009 |
| WO | WO-2010/050203 A1 | 5/2010 |
| WO | WO-2010/073260 A1 | 7/2010 |
| WO | WO-2010/090111 A1 | 8/2010 |
| WO | WO-2011/021085 A2 | 2/2011 |
| WO | WO-2011/040504 A1 | 4/2011 |
| WO | WO 2011/047199 | 4/2011 |
| WO | WO-2012/024006 A2 | 2/2012 |
| WO | WO 2013/015810 | 1/2013 |
| WO | WO 2013/058739 | 4/2013 |
| WO | WO 2013/062540 | 5/2013 |
| WO | WO-2014/025033 A1 | 2/2014 |
| WO | WO-2014/025034 A1 | 2/2014 |

OTHER PUBLICATIONS

Masahiro Yanagisawa, "Detection of Trace Organic Gas Using Molecular Sensor with Plasmon Antenna," Green Technology, Vo. 22, No. 6, Jun. 10, 2012, pp. 42-47, including at least partial English-language translation.

International Search Report dated Nov. 12, 2013, issued in International Application No. PCT/JP2013/071695.

International Search Report dated Nov. 5, 2013, issued in International Application No. PCT/JP2013/071696.

International Search Report dated Nov. 5, 2013, issued in International Application No. PCT/JP2013/071699.

International Search Report dated Nov. 5, 2013, issued in International Application No. PCT/JP2013/071700.

International Search Report dated Nov. 19, 2013, issued in International Application No. PCT/JP2013/071702.

International Search Report dated Nov. 12, 2013, issued in International Application No. PCT/JP2013/071703.

International Search Report dated Nov. 5, 2013, issued in International Application No. PCT/JP2013/071709.

International Search Report dated Nov. 5, 2013, issued in International Application No. PCT/JP2013/071710.

International Search Report dated Apr. 28, 2014, issued in International Application No. PCT/JP2014/052926.

International Search Report dated May 13, 2014, issued in International Application No. PCT/JP2014/052928.

K. Nakamoto et al., "Arrays of Metallic Nanopillars in Holes for Plasmonic Devices", Retrieved from the Internet: URL: http://www.rsc.org/images/LOC/2011/PDFs/Papers/596_0021.pdf, Oct. 6, 2011, XP055289892.

M. Tomohiko et al., "New Localized surface plasmon resonance sensor utilizing nanoimprinting technology", NSTI Nanotechnology Conference and Trade Show—NSTI Nanotech, vol. 1, May 11, 2006, p. 58-p. 61, XP009098538.

(56) References Cited

OTHER PUBLICATIONS

W. D. Li et al., "Three-deimensional cavity nanoantenna coupled plasmonic nanodots for ultrahigh and uniform surface-enhanced Raman scattering over large area", Optics Express, vol. 19, No. 5, Feb. 14, 2011, p. 3925-3936, XP002751299.

W. Zhang et al., "Giant and uniform fluorescence enhancement over large areas using plamonic nanodots in 3D resonant cavity nanoantenna by nanoimprinting", Nanotechnolgy, vol. 23, No. 22, May 10, 2012, p. 225301, XP020224099.

S. M. Wells et al., "Efficient disc on pillar substrates for surface enhanced Raman spectroscopy", Chemical Communications—Chemcom, vol. 47, No. 13, Jan. 1, 2011, p. 3814-p. 3816, XP055289549.

U.S. Office Action dated Aug. 25, 2016 that issued in U.S. Appl. No. 14/420,441 including Double Patenting Rejections on pp. 2-4.

U.S. Office Action dated Oct. 14, 2016 that issued in U.S. Appl. No. 14/420,510 including Double Patenting Rejections on pp. 2-14.

English Machine Translation of JP 2011-107032, Nishikawa et al., Jun. 2, 2011 as attached to U.S. Office Action dated Oct. 14, 2016 in U.S. Appl. No. 14/420,510.

\* cited by examiner

50nm

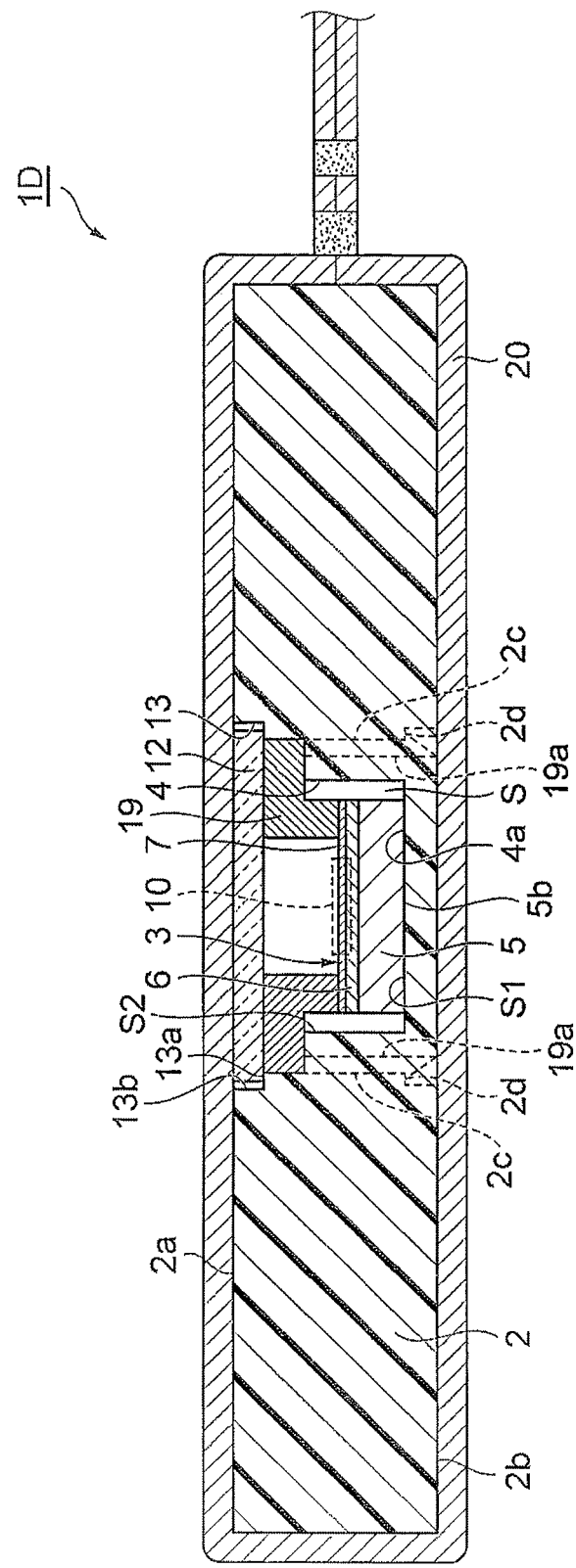

SURFACE-ENHANCED RAMAN SCATTERING UNIT INCLUDING INTEGRALLY FORMED HANDLING BOARD

TECHNICAL FIELD

The present invention relates to a surface-enhanced Raman scattering unit.

BACKGROUND ART

As a conventional surface-enhanced Raman scattering unit, one equipped with a minute metal structure configured to generate surface-enhanced Raman scattering (SERS) has been known (see, for example, Patent Literature 1 and Non Patent Literature 1). In such a surface-enhanced Raman scattering unit, when a sample to be subjected to Raman spectroscopy is brought into contact with the minute metal structure and is irradiated with excitation light in this state, surface-enhanced Raman scattering occurs, whereby Raman scattering light enhanced by about $10^8$ times, for example, is released.

CITATION LIST

Patent Literature

Patent Literature 1: Japanese Patent Application Laid-Open No. 2011-33518

Non Patent Literature

Non Patent Literature 1: "Q-SERS™ G1 Substrate", [online], Opto Science, Inc., [retrieved on Mar. 21, 2013]. Retrieved from the Internet: < URL: http://www.optoscience.com/maker/nanova/pdf/Q-SERS_G1.pdf>.

SUMMARY OF INVENTION

Technical Problem

The above-mentioned surface-enhanced Raman scattering unit has been problematic in that its minute metal structure serving as an optical function part is likely to deteriorate due to physical interference, adhesion of foreign matters, and the like.

It is therefore an object of the present invention to provide a surface-enhanced Raman scattering unit which can inhibit its optical function part from deteriorating due to physical interference, adhesion of foreign matters, and the like.

Solution to Problem

The surface-enhanced Raman scattering unit in accordance with one aspect of the present invention comprises an integrally formed handling board and a surface-enhanced Raman scattering element secured within a container space provided in the handling board so as to open to one side in a thickness direction of the handling board, the surface-enhanced Raman scattering element having a substrate arranged on an inner surface of the container space and an optical function part formed on the substrate, for generating surface-enhanced Raman scattering.

Since the surface-enhanced Raman scattering element is secured within the container space, this surface-enhanced Raman scattering unit inhibits the optical function part from deteriorating due to physical interference. Further, since the handling board is formed integrally, the optical function part is more inhibited from deteriorating due to adhesion of foreign matters such as adhesive components and chipping debris of members as compared with the case where the container space is formed by bonding a plurality of members with an adhesive, for example. Hence, this surface-enhanced Raman scattering unit can inhibit the optical function part from deteriorating due to physical interference, adhesion of foreign matters, and the like.

In the surface-enhanced Raman scattering unit in accordance with one aspect of the present invention, the container space may be a space within a depression provided on a principal surface on one side of the handling board. This configuration can stabilize the container space.

In the surface-enhanced Raman scattering unit in accordance with one aspect of the present invention, the container space may be a space on the inside of a ring-shaped wall part integrally formed on a principal surface on one side of the handling board. This configuration can make the handling board thinner.

The surface-enhanced Raman scattering unit in accordance with one aspect of the present invention may further comprise a cover arranged on the handling board so as to cover an opening of the container space. This configuration can more securely inhibit the optical function part from deteriorating due to physical interference.

In the surface-enhanced Raman scattering unit in accordance with one aspect of the present invention, the cover may be light-transmissive. When employing the container space as a cell (chamber) for a solution sample, this configuration can utilize the light-transmissive cover as a glass cover (cover slip) for transmitting excitation light therethrough in a Raman spectroscopic analyzer.

In the surface-enhanced Raman scattering unit in accordance with one aspect of the present invention, the cover may be arranged within a widened part provided in the opening and be restrained from moving in a direction perpendicular to the thickness direction. The cover may also be arranged on the inside of a projection integrally formed around the opening so as to surround the opening as seen in the thickness direction and be restrained from moving in a direction perpendicular to the thickness direction. These configurations can prevent the cover from shifting from the container space at the time of packing or using the surface-enhanced Raman scattering unit.

In the surface-enhanced Raman scattering unit in accordance with one aspect of the present invention, the handling board may integrally be formed from a resin. This configuration makes it possible to form the container space in the handling board easily and securely by integral molding. Further, since chipping is hard to occur, the optical function part can more securely be inhibited from deteriorating due to adhesion of chipping debris.

In the surface-enhanced Raman scattering unit in accordance with one aspect of the present invention, the surface-enhanced Raman scattering element may mechanically be secured within the container space. This configuration makes it unnecessary to use adhesives for securing the surface-enhanced Raman scattering element within the container space and thus can more securely inhibit the optical function part from deteriorating due to adhesion of adhesive components. Since no adhesives are used, it becomes unnecessary to apply resins and take their curing time, whereby the process can be simplified.

Advantageous Effects of Invention

The present invention can provide a surface-enhanced Raman scattering unit which can inhibit its optical function part from deteriorating due to physical interference, adhesion of foreign matters, and the like.

BRIEF DESCRIPTION OF DRAWINGS

FIG. 11 is a sectional view of the surface-enhanced Raman scattering unit in accordance with a fourth embodiment of the present invention.

DESCRIPTION OF EMBODIMENTS

Figure 1:
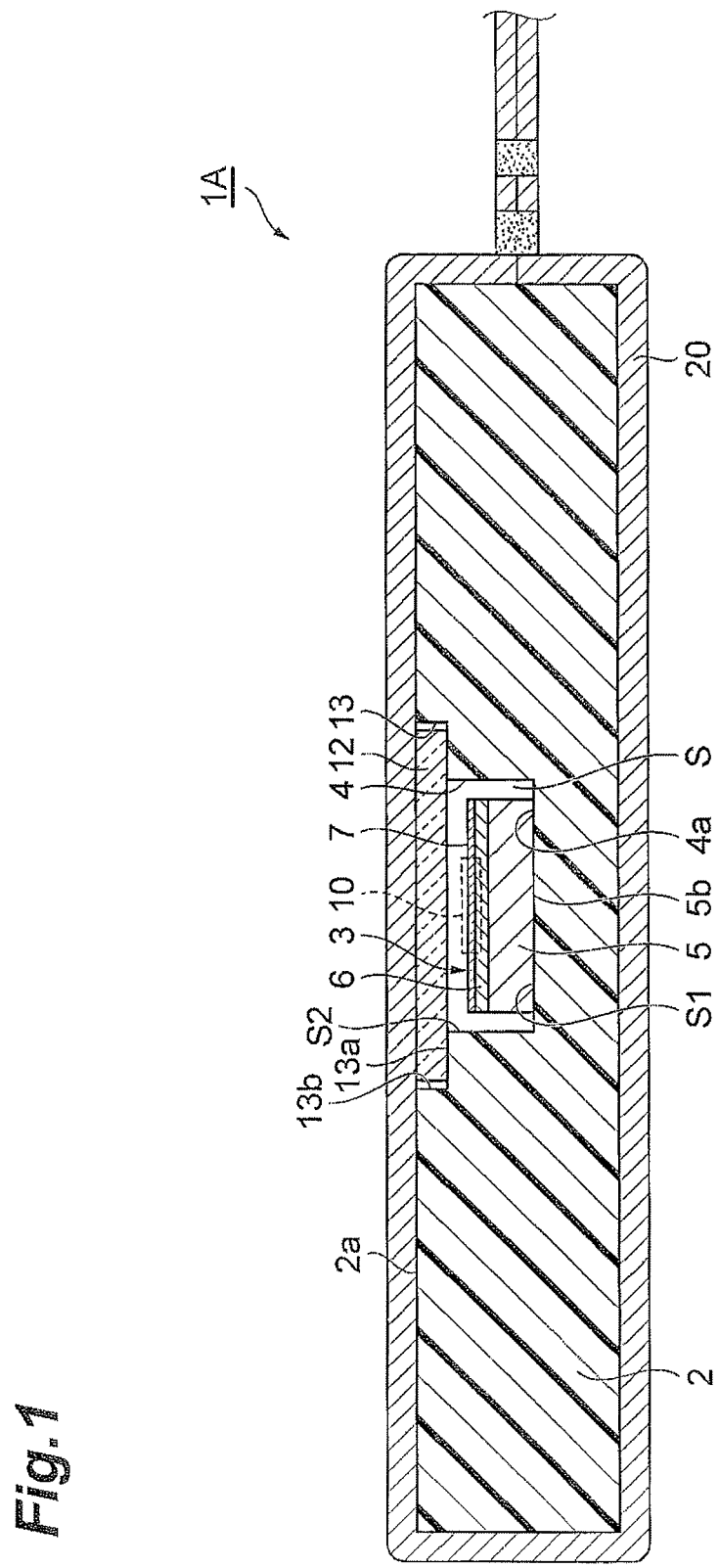
FIG. 1 is a sectional view of the surface-enhanced Raman scattering unit in accordance with a first embodiment of the present invention.

In the following, preferred embodiments of the present invention will be explained in detail with reference to the drawings. In the drawings, the same or equivalent parts will be referred to with the same signs while omitting their overlapping descriptions.

First Embodiment

Figure 2:
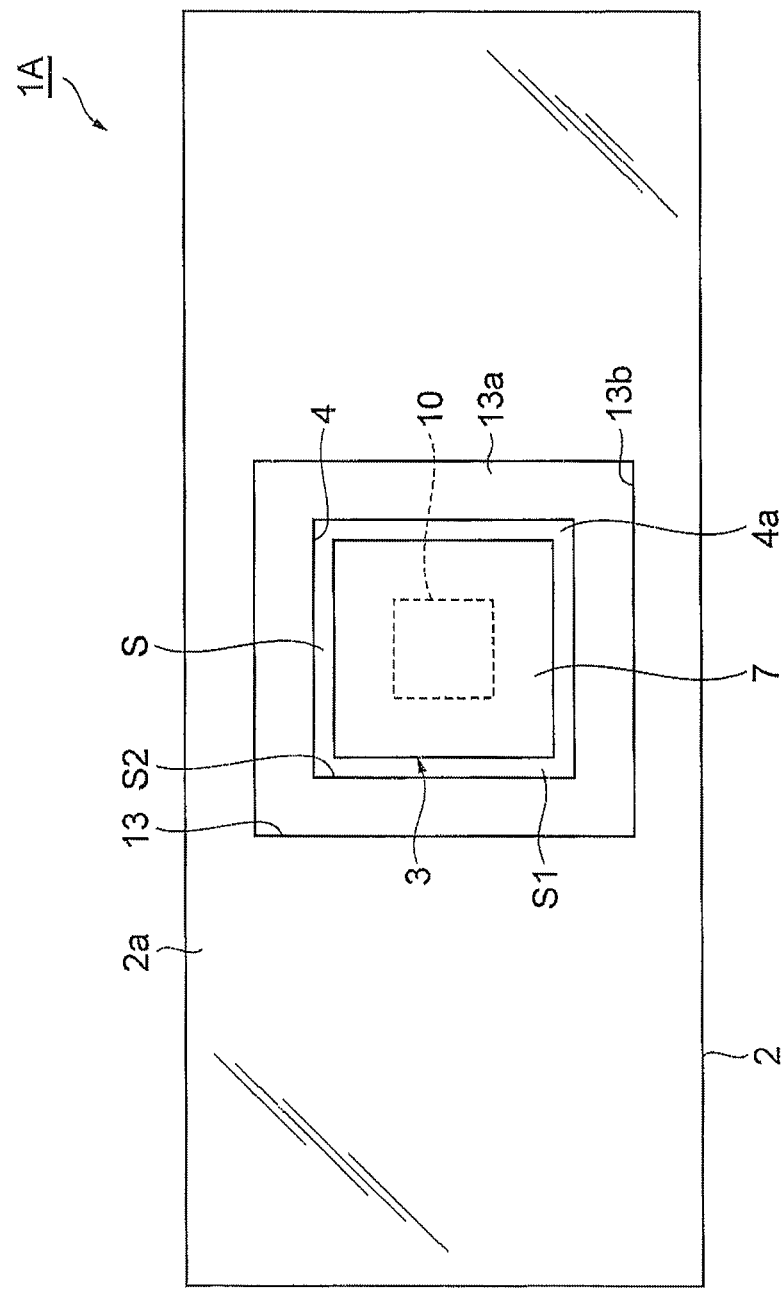
FIG. 2 is a plan view of the surface-enhanced Raman scattering unit of FIG. 1 without its package and cover.

As illustrated in FIGS. 1 and 2, a SERS unit (surface-enhanced Raman scattering unit) 1A comprises a handling board 2 integrally formed from a resin and a SERS element (surface-enhanced Raman scattering element) 3 supported by the handling board 2. A container space S is provided in the handling board 2 so as to open to one side in the thickness direction of the handling board 2. In the SERS unit 1A, the container space S is a space within a depression 4 provided on a front face (one principal surface) 2a of the handling board 2. By way of example, the handling board 2 is formed into a rectangular plate, while the depression 4 is formed integrally (seamlessly) into a rectangular parallelepiped. The handling board 2 like this is formed by integral molding with a resin, examples of which include polypropylene, PET, polycarbonate, styrol resins, ABS resins, polyethylene, PMMA, silicone, liquid crystal polymers, and defines the container space S by the same member made of the same material.

The SERS element 3 is secured within the container space S of the handling board 2. The SERS element 3 comprises a substrate 5 arranged on an inner surface S1 of the container space S (a bottom face 4a of the depression 4 in the SERS unit 1A), a molded layer 6 formed on the substrate 5, and a conductor layer 7 formed on the molded layer 6. By way of example, the substrate 5 is formed into a rectangular plate by silicon, glass, or the like and has an outer form on the order of several hundred μm×several hundred μm to several ten mm×several ten mm and a thickness on the order of 100 μm to 2 mm. A rear face 5b of the substrate 5 is secured to the inner surface S1 of the container space S by direct bonding, bonding with a metal such as solder, eutectic bonding, fusion bonding by irradiation with laser light and the like, anodic bonding, or bonding with a resin.

Figure 3:
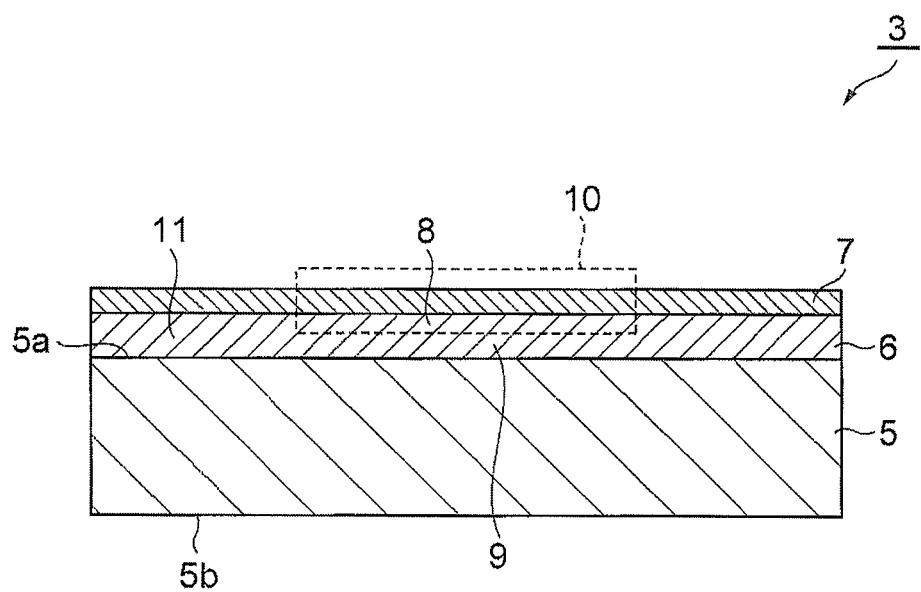
FIG. 3 is a sectional view of the surface-enhanced Raman scattering element of the surface-enhanced Raman scattering unit of FIG. 1.

As illustrated in FIG. 3, the molded layer 6 includes a fine structure part 8, a support part 9, and a frame part 11. The fine structure part 8, which is a region having a periodic pattern, is formed on a surface layer on the side opposite from the substrate 5 at a center part of the molded layer 6. A plurality of pillars, each having a thickness and height on the order of several nm to several hundred nm, are periodically arranged at a pitch on the order of several ten nm to several hundred nm in the fine structure part 8. By way of example, the fine structure part 8 has a rectangular outer form on the order of several hundred μm×several hundred μm to several ten mm×several ten mm when seen from one side in the thickness direction of the handling board 2. The support part 9, which is a region for supporting the fine structure part 8, is formed on a front face 5a of the substrate 5. The frame part 11, which is a region surrounding the support part 9 like a ring, is formed on the front face 5a of the substrate 5. By way of example, each of the support part 9 and frame part 11 has a thickness on the order of several ten nm to several ten μm. The molded layer 6 like this is integrally formed by molding a resin (examples of which include resins based on acrylics, fluorine, epoxy, silicone, and urethane, PET, polycarbonate, and inorganic/organic hybrid materials) or low-melting glass arranged on the substrate 5 by nanoimprinting, for example.

Figure 4:
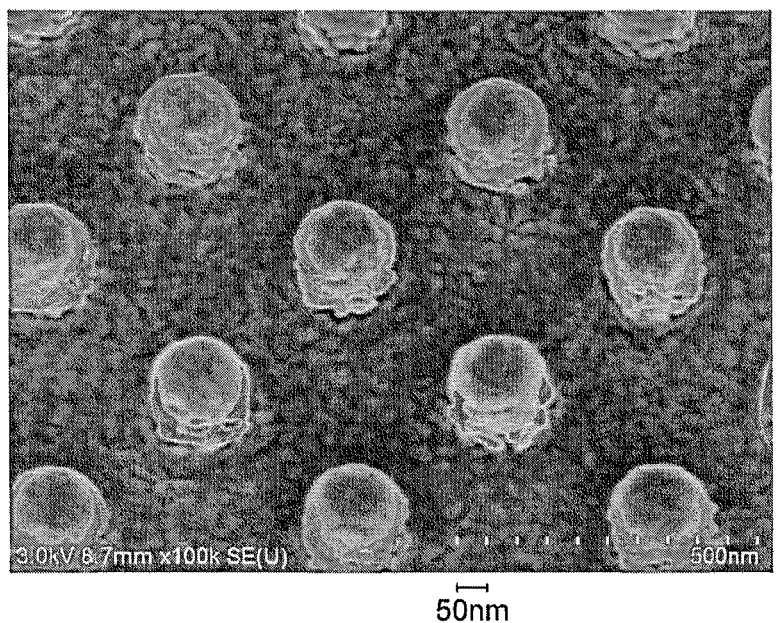
FIG. 4 is a SEM photograph of an optical function part in the surface-enhanced Raman scattering unit of FIG. 1.

The conductor layer 7 is formed so as to extend over the fine structure part 8 and frame part 11. In the fine structure part 8, the conductor layer 7 reaches the surface of the support part 9 exposed to the side opposite from the substrate 5. By way of example, the conductor layer 7 has a thickness on the order of several nm to several μm. The conductor layer 7 like this is formed by vapor-depositing a metal (Au, Ag, Al, Cu, Pt, or the like) on the molded layer 6 molded by nanoimprinting, for example. In the SERS element 3, the conductor layer 7 formed on the surface of the fine structure part 8 and the surface of the support part 9 exposed to the side opposite from the substrate 5 constructs an optical function part 10 which generates surface-enhanced Raman scattering. A SEM photograph of the optical function part 10 is shown for reference. The optical function part shown in FIG. 4 is one in which Au was vapor-deposited as a conductor layer so as to yield a thickness of 50 nm in a fine structure part made of a nanoimprinting resin having a plurality of pillars (each having a diameter of 120 nm and a height of 180 nm) periodically arranged at a predetermined pitch (center line distance of 360 nm).

As illustrated in FIG. 1, the SERS unit 1A further comprises a light-transmissive cover 12. The cover 12 is arranged on the handling board 2 so as to cover an opening S2 of the container space S. More specifically, the cover 12 is arranged within a widened part 13 provided in the opening S2 of the container space S. The widened part 13 is made wider than the depression 4 not only in the longitudinal direction of the handling board 2 but also in a direction perpendicular to the longitudinal direction and thickness direction of the handling board 2. The cover 12 is arranged on a bottom face 13a of the widened part 13 in a detachable state (i.e., a state not secured with adhesives and the like)

and is restrained by a side face 13b of the widened part 13 from moving in directions perpendicular to the thickness direction of the handling board 2. By way of example, the cover 12 is formed into a rectangular plate from glass or the like and has an outer form on the order of 18 mm×18 mm and a thickness on the order of 0.15 mm.

Thus constructed SERS unit 1A is packed in a bag-shaped package 20 before used. In this state, the container space S of the SERS unit 1A is made an inert space by raising its degree of vacuum, being filled with an inert gas, or constructing the package 20 in an atmosphere with less foreign matters and impurities. This prevents the surface-enhanced Raman scattering effect from deteriorating (e.g., the surface-enhanced Raman scattering effect from deteriorating due to foreign matters and impurities attached to the optical function part 10) before used. The SERS unit 1A may also be packed in the package 20 in a state where the optical function part 10 is dipped in a chemical solution having a cleaning effect such as alcohol. In this case, the package 20 is unsealed when used, whereby the chemical solution is removed from the optical function part 10.

Figure 5:
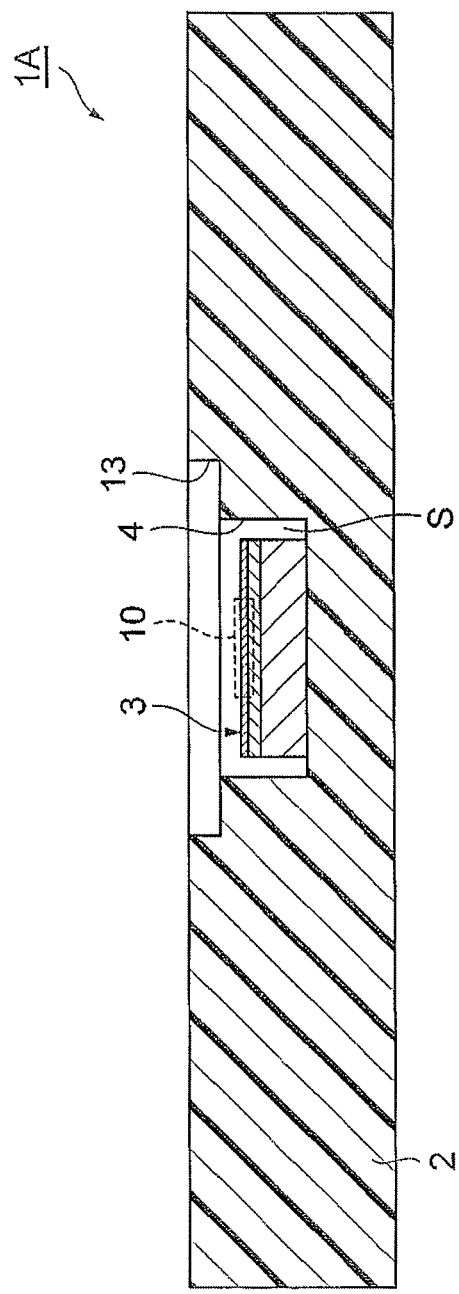
FIG. 5 is a sectional view illustrating a step of using the surface-enhanced Raman scattering unit of FIG. 1.
Figure 6:
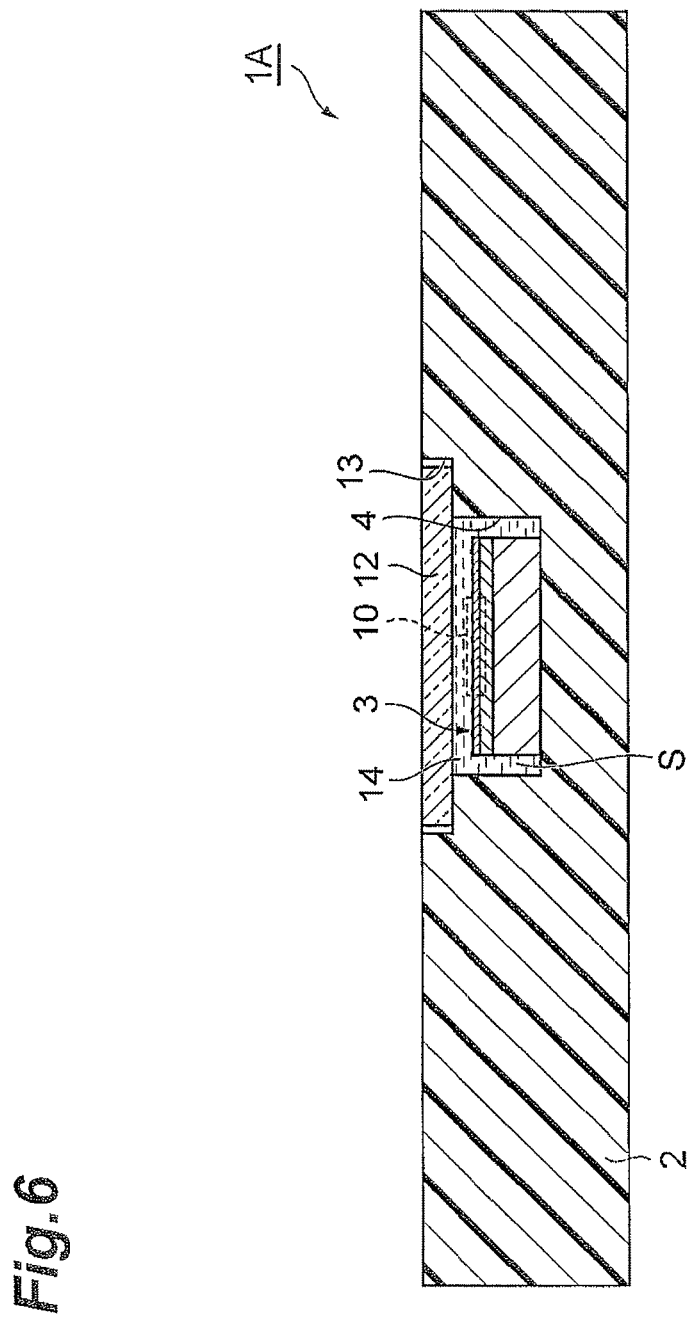
FIG. 6 is a sectional view illustrating a step of using the surface-enhanced Raman scattering unit of FIG. 1.

A method for using the SERS unit 1A will now be explained. First, the package 20 is unsealed, so as to expose the container space S irreversibly, and the cover 12 is taken out of the handling board 2, so that the optical function part 10 of the SERS element 3 is exposed to the external atmosphere as illustrated in FIG. 5. Subsequently, as illustrated in FIG. 6, a sample 14 of a solution (or a dispersion of a powder sample in a solution such as water or ethanol) is dropped into the container space S with a pipette or the like, so as to be arranged on the optical function part 10. Then, for reducing the lens effect, the cover 12 is arranged within the widened part 13 of the handling board 2 and brought into close contact with the solution sample 14.

Next, the SERS unit 1A is set in a Raman spectroscopic analyzer, and the solution sample 14 arranged on the optical function part 10 is irradiated with excitation light through the cover 12. This generates surface-enhanced Raman scattering at the interface between the optical function part 10 and solution sample 14, whereby surface-enhanced Raman scattering light derived from the solution sample 14 is enhanced by about $10^8$ times, for example, and released. Thus, the Raman spectroscopic analyzer enables Raman spectroscopy with high sensitivity and high accuracy.

Not only the above-mentioned method, but the following methods may also be used for arranging the sample on the optical function part 10. For example, while holding the handling board 2, the SERS element 3 may be dipped in and lifted from the solution sample (or a dispersion of a powder sample in a solution such as water or ethanol), and then the sample may be blown to dry. A minute amount of the solution sample (or a dispersion of a powder sample in a solution such as water or ethanol) may be dropped onto the optical function part 10 and left to dry. A powder sample may be dispersed as it is on the optical function part 10. In these cases, it is not necessary for the cover 12 to be arranged at the time of measurement.

Effects exhibited by the SERS unit 1A will now be explained. First, since the SERS element 3 is secured within the container space S, the optical function part 10 is inhibited from deteriorating due to physical interference before and during using the SERS unit 1A. Further, since the handling board 2 is formed integrally, the optical function part 10 is more inhibited from deteriorating due to adhesion of foreign matters such as adhesive components and chipping debris of members before using the SERS unit 1A in particular as compared with the case where the container space S is formed by bonding a plurality of members with an adhesive, for example. Hence, the SERS unit 1A can inhibit the optical function part 10 from deteriorating due to physical interference, adhesion of foreign matters, and the like.

Since the SERS element 3 is secured within the container space S, the container space S can be utilized as a cell (chamber) for the solution sample 14. This can save the trouble of setting a spacer for reserving the solution sample 14 on the handling board 2. In addition, since the handling board 2 defining the container space S is formed integrally, the solution sample 14 can be prevented from leaking and oozing.

Since the container space S is a space within the depression 4 provided on the front face 2a of the handling board 2, keeping the thickness of the handling board 2 so as to restrain it from deforming can stabilize the container space S.

Since the cover 12 is arranged on the handling board 2 so as to cover the opening S2 of the container space S, the optical function part 10 can more securely be inhibited from deteriorating due to physical interference, e.g., the package 20 is prevented from deforming such as to come into contact with the optical function part 10 when the package 20 containing the SERS unit 1A is vacuumed. Further, when vacuuming the package 20 containing the SERS unit 1A, only the container space S as a minimal space is required to be vacuumed, whereby the container space S can efficiently be made a highly clean space.

Since the cover 12 is light-transmissive, when employing the container space S as a cell (chamber) for the solution sample 14, the cover 12 can be utilized as a glass cover (cover slip) for transmitting excitation light therethrough in a Raman spectroscopic analyzer.

Since the cover 12 is arranged within the widened part 13 provided in the opening S2 of the container space S and is restrained from moving in directions perpendicular to the thickness direction, the cover 12 can be prevented from shifting from the container space S at the time of packing or using the SERS unit 1A.

Since the handling board 2 is integrally formed from a resin, the container space S can be formed in the handling board 2 easily and securely by integral molding. This also makes it harder for chipping to occur, whereby the optical function part 10 can more securely be inhibited from deteriorating due to adhesion of chipping debris. Embossing the outer surface of the handling board 2 or using a resin having a light-absorbing color for a material of the handling board 2 can further inhibit stray light from occurring at the time of Raman spectroscopic analysis.

Figure 7:
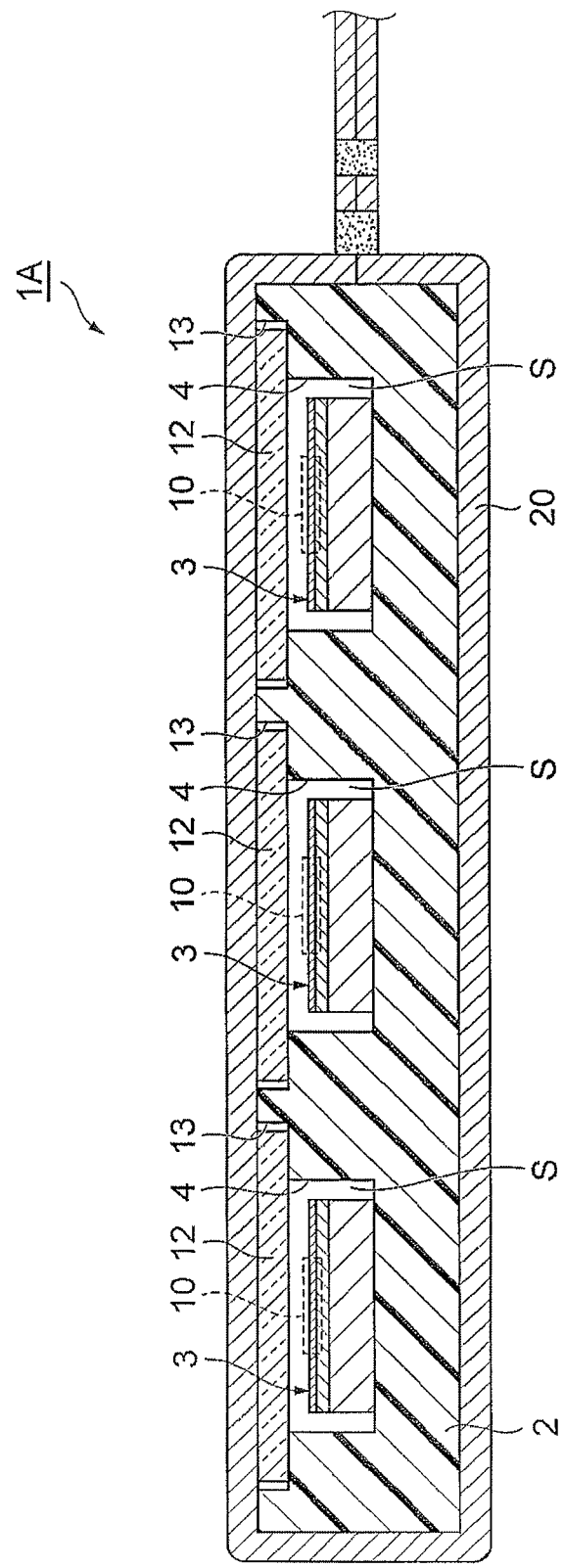
FIG. 7 is a sectional view of a modified example of the surface-enhanced Raman scattering unit of FIG. 1.

Modified examples of the above-mentioned SERS unit 1A will now be explained. In the SERS unit 1A, as illustrated in FIG. 7, one handling board 2 may be provided with a plurality of container spaces S, each having the SERS element 3 secured therewithin. This configuration enables one handling board 2 to measure a plurality of kinds of samples. It can also save the trouble of replacing the SERS unit 1A and so forth at the time of measurement. The plurality of container spaces S may be arranged either one-dimensionally or two-dimensionally with respect to one handling board 2.

Figure 8:
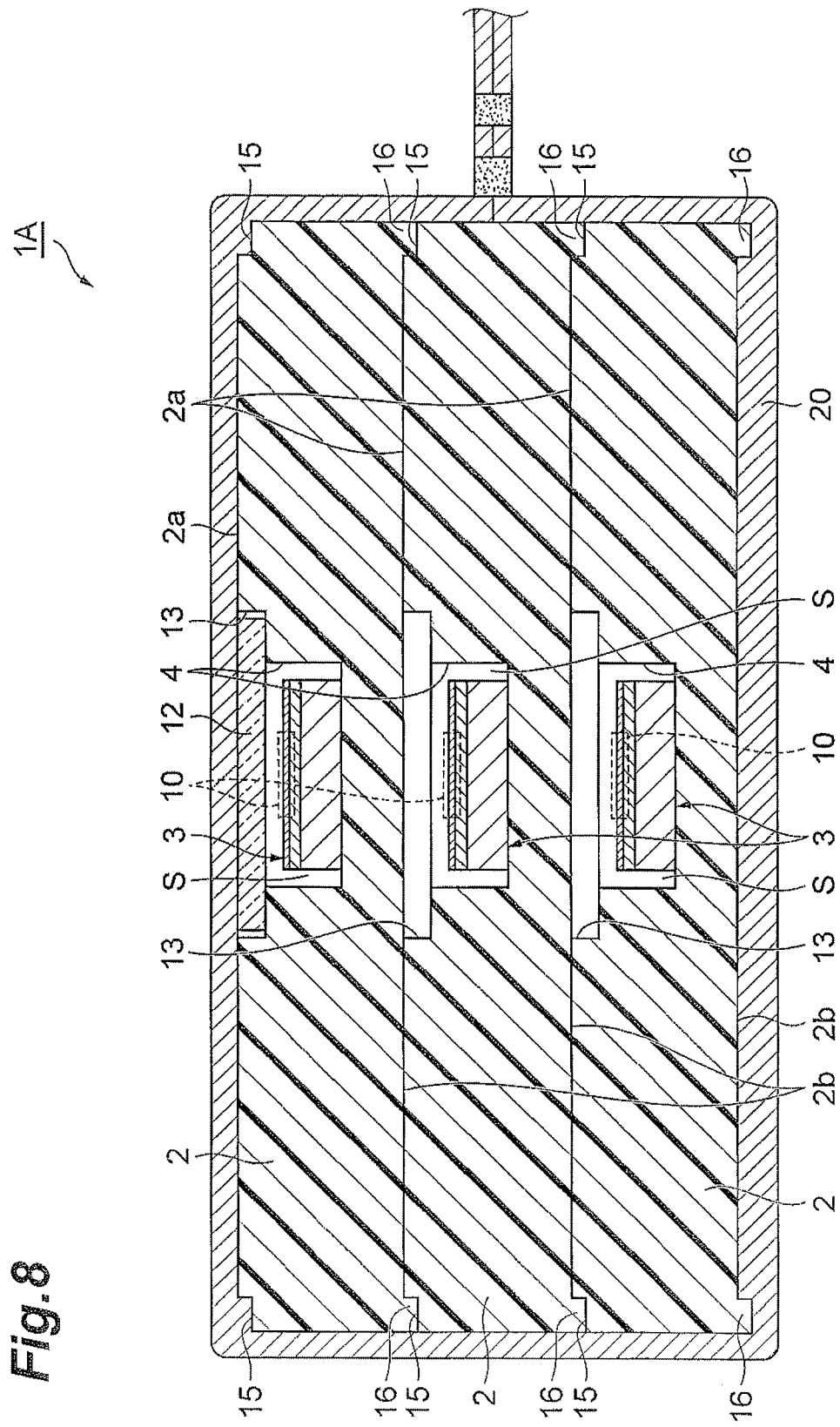
FIG. 8 is a sectional view of a modified example of the surface-enhanced Raman scattering unit of FIG. 1.

In the SERS unit 1A, as illustrated in FIG. 8, a plurality of handling boards 2 may be stacked in their thickness direction, the SERS element 3 being secured within the container space S provided in each handling board 2. This configuration enables one package 20 to seal a plurality of handling boards 2 against the external atmosphere. From the viewpoint of preventing the package 20 from deforming such as to come into contact with the optical function part 10 when vacuuming the package 20 containing the SERS unit 1A, the cover 12 is not required to be arranged on the handling board 2 having the container S whose opening S2 is covered with another handling board 2.

Further, in this case, two handling boards 2 adjacent to each other in their thickness direction may restrain each other from moving in directions perpendicular to the thickness direction by placing a projection 16 integrally formed in one handling board 2 into a recess 15 provided in the other handling board 2. In the SERS unit 1A illustrated in FIG. 8, recesses 15 are provided in four sides along the outer edges of the front face 2a of the handling board 2, while projections 16 are integrally formed on four sides along the outer edges of the rear face 2b of the handling board 2. This configuration can prevent the stacked handling boards 2 from shifting from each other at the time of packing the SERS unit 1A, so as to secure the packing.

Second Embodiment

Figure 9:
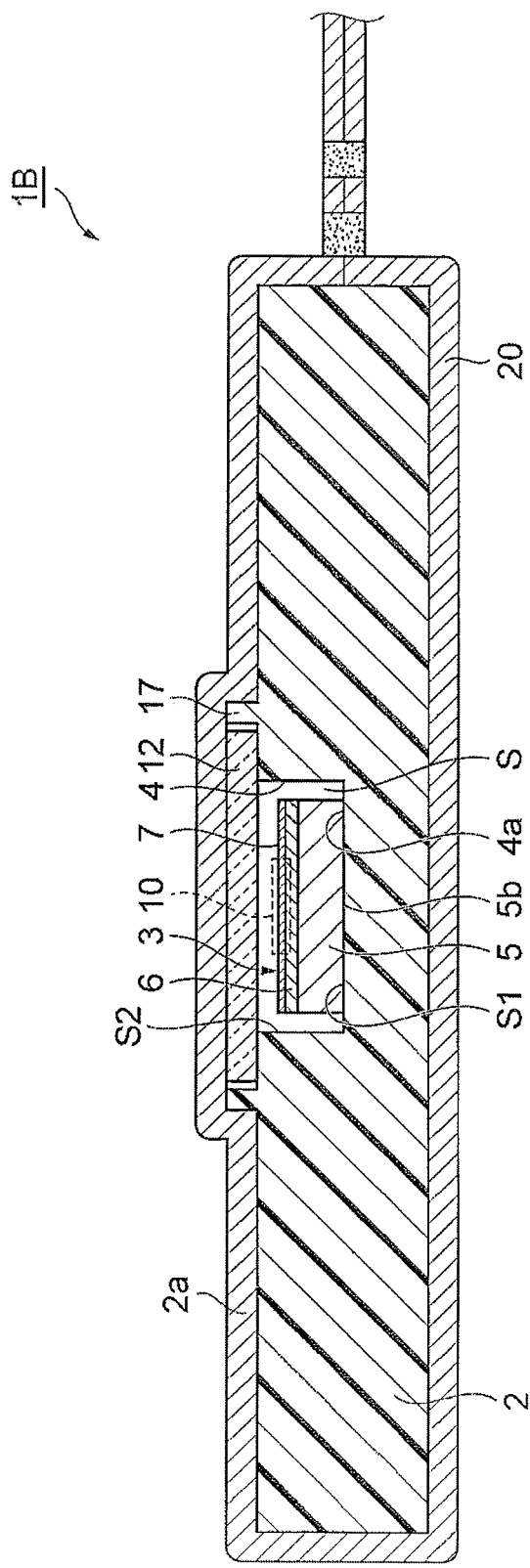
FIG. 9 is a sectional view of the surface-enhanced Raman scattering unit in accordance with a second embodiment of the present invention.

As illustrated in FIG. 9, a SERS unit 1B differs from the above-mentioned SERS unit 1A mainly in that it is arranged on the inside of a ring-shaped projection 17 which is integrally formed on the front face 2a of the handling board 2. In the SERS unit 1B, the projection 17 is integrally formed around the opening S2 of the container space S so as to surround the opening S2 when seen in the thickness direction of the handling board 2. The cover 12 is arranged on the front face 2a on the inside of the projection 17 and is restrained by the projection 17 from moving in directions perpendicular to the thickness direction of the handling board 2. This configuration can prevent the cover 12 from shifting from the container space S at the time of packing and using the SERS unit 1A as in the above-mentioned. SERS unit 1A. As compared with the above-mentioned SERS unit 1A, the opening S2 of the container space S is free of the widened part 13 and accordingly can improve the strength of the handling board 2. The projection 17 is not limited to one formed into a ring, but may surround the opening S2 of the container space S while being divided into a plurality of parts.

Third Embodiment

Figure 10:
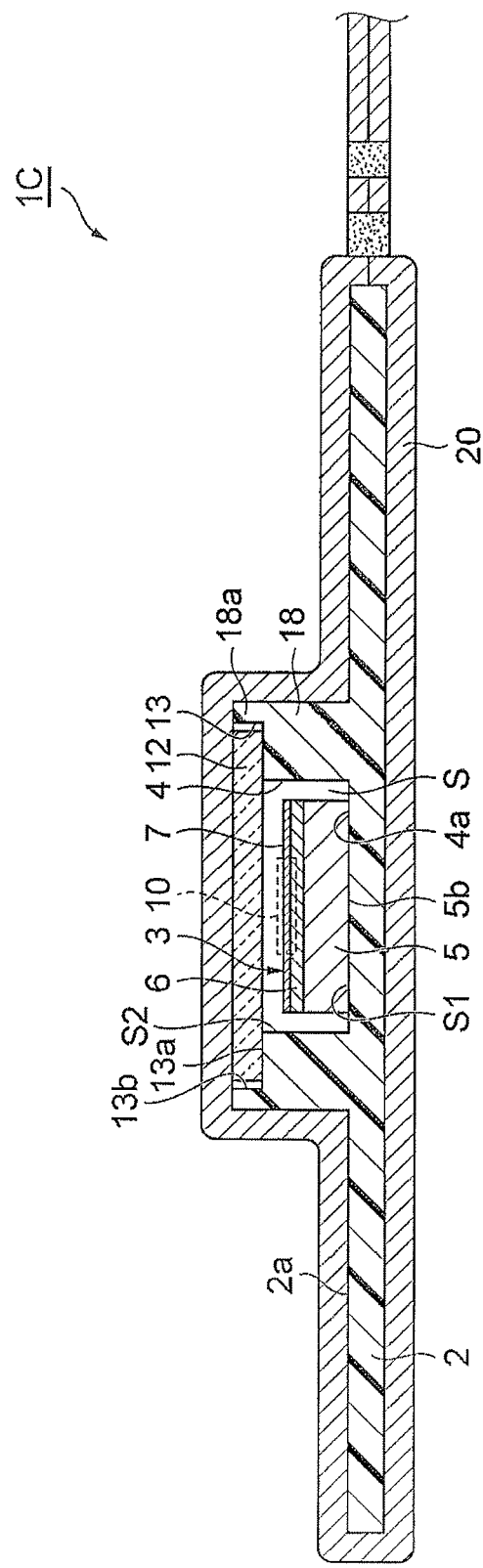
FIG. 10 is a sectional view of the surface-enhanced Raman scattering unit in accordance with a third embodiment of the present invention.

As illustrated in FIG. 10, a SERS unit 1C differs from the above-mentioned SERS unit 1A mainly in that the container space S is arranged on the inside of a ring-shaped wall part 18 which is integrally formed on the front face 2a of the handling board 2. In the SERS unit 1C, the SERS element 3 is secured onto the front face 2a on the inside of the ring-shaped wall part 18. The cover 12 is arranged within the widened part 13 provided in an end part 18a of the ring-shaped wall part 18 on the side opposite from the handling board 2. This configuration can make the handling board 2 thinner. This leads to cutting down the cost of materials for forming the handling board 2. When holding the handling board 2 with securing members such as slide clips of a microscope, the thickness of the handling board 2 can be adjusted according to the securing members regardless of the size of the container space S. Since the SERS element 3 is surrounded by the ring-shaped wall part 18, securing members such as slide clips of a microscope can also be prevented from coming into contact with the SERS element 3.

Fourth Embodiment

As illustrated in FIG. 11, a SERS unit 1D differs from the above-mentioned SERS unit 1A mainly in that the SERS element 3 is mechanically secured within the container space S. In the SERS unit 1D, the SERS element 3 is secured within the container space S not with an adhesive but by a securing member 19. More specifically, the securing member 19 is formed into a ring and has a plurality of claws 19a extending toward the rear face 2b of the handling board 2. The securing member 19 like this is formed by integral molding with a resin, for example. The securing member 19 is arranged within the container space S and in contact with the conductor layer 7 of the SERS element 3 so as to surround the optical function part 10 when seen in the thickness direction of the handling board 2. In this state, each claw 19a of the securing member 19 engages a stepped part 2d of a through hole 2c provided in the handling board 2. This configuration makes it unnecessary to use adhesives for securing the SERS element 3 within the container space S and thus can more securely inhibit the optical function part 10 from deteriorating due to adhesion of adhesive components.

While the first to fourth embodiments of the present invention are explained in the foregoing, the present invention is not limited to the above-mentioned embodiments. For example, the material for the handling board 2 is not limited to resins, but may be low-melting glass, ceramics, and the like. When the material for the handling board 2 is low-melting glass, the handling board can be formed by integral molding as in the case of resins. When the material for the handling board 2 is a ceramic, the handling board can be formed by firing. Without being restricted to those mentioned above, various materials and forms can be employed for the constituents of the SERS units 1A to 1D. By the ring is meant not only circular rings, but also other forms of rings such as rectangular rings.

The fine structure part 8 may be formed on the front face 5a of the substrate 5 either directly or indirectly with the support part 9, for example, interposed therebetween. The conductor layer 7 is not limited to the one directly formed on the fine structure part 8, but may be formed indirectly on the fine structure part 8 with a layer such as a buffer metal (Ti, Cr, or the like) layer for improving the adhesion of a metal to the fine structure part 8, for example, interposed therebetween.

INDUSTRIAL APPLICABILITY

The present invention can provide a surface-enhanced Raman scattering unit which can inhibit its optical function part from deteriorating due to physical interference, adhesion of foreign matters, and the like.

REFERENCE SIGNS LIST 1A, 1B, 1C, 1D: SERS unit (surface-enhanced Raman scattering unit); 2: handling board; 2a: front face (principal surface on one side); 3: SERS element (surface-enhanced Raman scattering element); 4: depression; 5: substrate; 10: optical function part; 12: cover; 13: widened part; 17: projection; 18: ring-shaped wall part; S: container space; S1: inner surface; S2: opening.

The invention claimed is:
1. A surface-enhanced Raman scattering unit comprising:
an integrally formed handling board;

a surface-enhanced Raman scattering element secured within a container space provided in the handling board so as to open to one side along a thickness direction of the handling board;
wherein the surface-enhanced Raman scattering element has:
a substrate arranged on a bottom surface of the container space; and
an optical function part formed on the substrate, for generating surface-enhanced Raman scattering,
wherein the substrate is secured to the bottom surface, and is interposed between the bottom surface and the optical function part, and is spaced from a side surface of the container space;
a bag-shaped package packing the handling board before use, and configured to irreversibly expose the container space when used, wherein the inside of the bag-shaped package is vacuumed before use; and
a member having an outer side surface extending along the thickness direction and positioned outside the optical function part as seen in the thickness direction, wherein the outer side surface faces an inner surface of the handling board.

2. A surface-enhanced Raman scattering unit according to claim 1, wherein the container space is a space within a depression provided on a principal surface on the one side of the handling board.

3. A surface-enhanced Raman scattering unit according to claim 1, wherein the container space is a space on the inside of a ring-shaped wall part integrally formed on a principal surface on the one side of the handling board.

4. A surface-enhanced Raman scattering unit according to claim 1, wherein the member is a securing member for mechanically securing the surface-enhanced Raman scattering element within the container space, and further comprising a cover arranged on the handling board so as to cover an opening of the container space.

5. A surface-enhanced Raman scattering unit according to claim 4, wherein the cover is light-transmissive.

6. A surface-enhanced Raman scattering unit according to claim 4, wherein the cover is arranged within a widened part provided in the opening and is restrained from moving in a direction perpendicular to the thickness direction.

7. A surface-enhanced Raman scattering unit according to claim 4, wherein the cover is arranged on the inside of a projection integrally formed around the opening so as to surround the opening as seen in the thickness direction and is restrained from moving in a direction perpendicular to the thickness direction.

8. A surface-enhanced Raman scattering unit according to claim 1, wherein the handling board is integrally formed from a resin.

9. A surface-enhanced Raman scattering unit according to claim 8, wherein the resin has a light-absorbing color.

10. A surface-enhanced Raman scattering unit according to claim 1, wherein the member is a cover arranged on the handling board so as to cover an opening of the container space.

11. A surface-enhanced Raman scattering unit according to claim 10, wherein the cover is light-transmissive.

12. A surface-enhanced Raman scattering unit according to claim 10, wherein the cover is arranged within a widened part provided in the opening and is restrained from moving in a direction perpendicular to the thickness direction.

13. A surface-enhanced Raman scattering unit according to claim 10, wherein the cover is arranged on the inside of a projection integrally formed around the opening so as to surround the opening as seen in the thickness direction and is restrained from moving in a direction perpendicular to the thickness direction.

* * * * *